United States Patent [19]
Asada et al.

[11] Patent Number: 6,162,458
[45] Date of Patent: Dec. 19, 2000

[54] PATCH FOR BEAUTIFICATION

[75] Inventors: Masanori Asada; Yuri Shibata; Yoshiyuki Nagaoka, all of Nishinomiya, Japan

[73] Assignee: Nagaoka & Co., Ltd., Japan

[21] Appl. No.: 09/392,008

[22] Filed: Sep. 8, 1999

Related U.S. Application Data

[63] Continuation-in-part of application No. 09/193,546, Nov. 17, 1998.

[51] Int. Cl.⁷ .............................. A61L 15/16; A61K 7/00; A61K 39/385
[52] U.S. Cl. ..................... 424/448; 424/401; 424/195.1
[58] Field of Search ............................. 424/448, 195.1, 424/401

[56] References Cited

U.S. PATENT DOCUMENTS

| | | | |
|---|---|---|---|
| 441,009 | 11/1890 | Jenkins . | |
| 4,205,685 | 6/1980 | Yoshida et al. | 128/399 |
| 4,695,465 | 9/1987 | Kigasawa et al. | 424/449 |
| 4,795,638 | 1/1989 | Ayache et al. . | |
| 5,512,277 | 4/1996 | Uemura et al. | 424/78.03 |
| 5,578,312 | 11/1996 | Parrinello . | |
| 5,723,138 | 3/1998 | Bae et al. | 424/401 |
| 5,780,047 | 7/1998 | Kamiya et al. . | |

*Primary Examiner*—Diana Dudash
*Assistant Examiner*—Alysia Berman
*Attorney, Agent, or Firm*—Webb Ziesenheim Logsdon Orkin & Hanson, P.C.

[57] ABSTRACT

The present invention provides a patch for beautification comprising a support and an adhesive mass, wherein the adhesive mass contains active components that have a skin-refreshing effect, a skin-clearing effect and/or a slenderizing effect. The active component of the patch for beautification of the present invention having at least one of a skin-refreshing effect, a skin-clearing effect and a slenderizing effect can effectively and sustainedly act on a desired site of the body.

6 Claims, No Drawings

PATCH FOR BEAUTIFICATION

CROSS-REFERENCE TO RELATED APPLICATION

This is a continuation-in-part of U.S. patent application Ser. No. 09/193,546 filed Nov. 17, 1998.

BACKGROUND OF THE INVENTION

1. Field of the Invention

The present invention relates to a patch for beautification having a skin-refreshing effect, a skin-clearing effect and/or a slenderizing effect.

2. Description of the Related Art

Plant extract is believed to have a skin-refreshing effect, a skin-clearing effect and/or a slenderizing effect. A lotion, gel or cream containing the plant extract has already been on the market. However, such conventional products have the following problems: for example, the effect is not clear; the effect is not sustained enough; the product is sticky when it is used; and clothes are dirtied by the product. Thus, a product that contains the active component(s) having the above-mentioned effects which acts on a desired site of the body effectively and sustainedly, and is handled with ease, has not yet been obtained.

SUMMARY OF THE INVENTION

The object of the present invention is to solve the above mentioned problems and, thereby, to provide a product containing the active component(s) that has a skin-refreshing effect, skin-clearing effect and/or a slenderizing effect and acting on a desired site of the body effectively and sustainedly. Further, the object of the present invention is to provide a product having the above-mentioned effects and which is easily handled.

According to the present invention, a patch for beautification comprising a support and an adhesive mass, wherein the patch has a skin-refreshing effect, a skin-clearing effect and/or a slenderizing effect, and wherein the adhesive mass contains plant extracts, seaweed extract and extract of peppermint, can be provided.

In a preferred embodiment, the adhesive mass contains extract of ginseng, extract of *Hedera helix L*, extract of *Matricaria chamomilla L*, extract of *Rosmarinus officinalis L*, seaweed extract and l-menthol as active components.

In another preferred embodiment, the adhesive mass further contains animal oil, mushroom extract and extract of red pepper as active components.

In another preferred embodiment, the adhesive mass contains extract of ginseng, extract of adlay or extract of bud Japanese honeysuckle as the plant extract, extract of kelp or extract of wakame seaweed as the seaweed extract, mink oil or horse oil as the animal oil, extract of vegetable wasps, extract of chlorella or extract of shiitake mushroom as the mushroom extract and extract of natural peppermint or extract of red pepper as the extract of pepper.

In another preferred embodiment, the patch comprises extract of ginseng, extract of kelp, mink oil, extract of yeast, natural peppermint oil, and natural salt as active components.

In another preferred embodiment, the patch is in the form of a cataplasm, plaster or tape.

In a preferred embodiment, the patch can be applied to or can swathe a desired site of the body.

Thus, the invention described herein makes possible the advantages of providing a patch that is easy to handle and contains the active component(s) that has a skin-refreshing effect, a skin-clearing effect and/or a slenderizing effect and acts on a desired site of the body effectively and sustainedly.

These and other advantages of the present invention will become apparent to those skilled in the art upon reading and understanding the following detailed description.

DETAILED DESCRIPTION OF THE INVENTION

The active component contained in the adhesive mass of the patch of the present invention has a skin-refreshing effect, a skin-clearing effect and/or slenderizing effect. Examples of the component include seaweed extract, vegetable oil, plant extract, animal oil, animal extract, mushroom extract, algae extract, microorganism extract, metabolites of microorganisms, seawater compositions, mud and so on.

As the seaweed extract, extracts of kelp (*Laminaria japonica*), wakame seaweed (*Undaria pinnatifida*), fucus (*Fucus evanescens*), hijiki seaweed (*Hizikia fusiformis*) and so on can be used.

As the vegetable oil, sesame oil and so on can be used.

As the plant extract, extracts of ginseng, peppermint, adlay (*Coix lacrima-jobi* var. *maiyuen*), Japanese honeysuckle, *Hedera helix L, Matricaria chamomilla L, Rosmarinus officinalis L*, pepper including red pepper, *Centella asiatica*, tea and so on can be used.

As the animal oil and animal extract, mink oil, horse oil and extract of abyssal shark can be used.

As the mushroom extract, extracts of shiitake mushrooms (*Lentinus edodes*), polypore, flammulina, vegetable wasps, koji mold (Aspergillus) and so on can be used.

As the algae extract, extracts of Chlorella, Chramydomonas, Cynecococcus, Spirulina and so on can be used.

As the microorganism extract, extracts of yeast, Lactobacillus and so on can be used.

As the metabolites of microorganisms, poly amino acid, lipo amino acid, surfactin, kojic acid, hiarulonic acid and so on can be used.

As the seawater compositions, bittern, natural salt and so on can be used.

As the mud, mud of the Dead Sea and so on can be used.

Among these, the seaweed extract, plant extract, mushroom extract, microorganism extract, seawater compositions or mud are preferred. The extracts of kelp, fucus, hijiki seaweed, peppermint, Japanese honeysuckle, red pepper, Centella asiatica, polypore, vegetative wasps, koji mold (Aspergillus), yeast or the like, or bittern are especially preferred. The active component can be used alone or in combination.

As a method for extracting the active component from the above raw materials, any suitable method can be used. For example, a raw material can be added to water or hot water and crushed by a homogenizer such as a Waring blender or ultrasonic crusher so as to extract the active component, and the residue can be centrifuged and/or filtrated to obtain the aimed extract. The extract can also be obtained by extraction with steam distillation, or by using a solvent such as ethanol or ethylacetate, followed by removing the solvent.

As a base component for the adhesive mass used in the patch for beautification of the present invention, any suitable base can be used. For example, gelatin, carboxymethylcellulose, methylcellulose, sodium polyacrylate, kaolin, polyvinylalcohol, polyvinylpyrrolidone, glycerin, propyleneglycol, rubber, resin, and plastics such as styrene-isoprene copolymer and polybutadiene, and so on can be used.

As the base component of the plaster, rubber, resin, and plastics such as styrene-isoprene copolymer and poly butadiene, can be used.

The adhesive mass can be obtained by mixing or kneading the above base and the above active component. Any suitable mixing or kneading method can be used depending on the characteristics of the adhesive mass and the active component.

The additive amount of the active component to the adhesive mass varies depending on the nature of the active component. However, it is usually from about 0.01% by weight to about 10% by weight, and preferably from about 0.05% by weight to about 5% by weight, on the basis of the total weight of the adhesive mass.

To the adhesive mass of the patch for beautification of the present invention, in addition to the above active component, perfumes such as rose oil, vanilla essence and so on can be optionally added.

The patch for beautification of the present invention can be prepared by spreading the adhesive mass on a support. As the support used in the present invention, for example, woven fabric such as flannel, non-woven fabric, foamed film, synthetic resin film, and so on can be used.

The patch for beautification of the present invention can be in the form of a cataplasm, plaster or tape. The term "cataplasm", "plaster" or "tape" used herein is referred to as it is used by those skilled in the art. The cataplasm is an external preparation made by kneading the active component and the base into a mud-like form, followed by spreading on the support, and can be used in the same manner as a compress. The plaster is an external preparation made by kneading a sticky base and the active component, followed by spreading on the support, and can be applied to the skin. The tape is a kind of plaster in which the width of the plaster is narrow.

The patch for beautification of the present invention can be applied to or can swathe a desired site of the body such as the arm, the abdominal region, the buttocks, the femoral region, the calf, or the ankles. The ability of adhesion to the skin of the adhesive mass can be supplemented by enlarging the patch. Further, the patch for beautification of the present invention can be made in any suitable form so as to fit the shape of the site to be applied.

The patch for beautification of the present invention can be used mainly for the beauty purposes of skin refreshing, skin clearing and/or slenderizing of the body; however, the patch can also be used in cases where the slenderizing of the body is desired in view of medical treatment.

For the purpose of slenderizing the body, the patch can tightly swathe a desired site or be slightly fixed with a belt or tape with a broader width so as to cover the applied or swathed patch. By these applications, the effect of slenderizing the body can be strengthened.

Further, in order to strengthen the effect of skin refreshing, skin clearing and/or slenderizing of the body, it is possible to warm the patch for beautification of the present invention so as to use it as a hot patch. For example, the patch of the present invention can be warmed without any special equipments; for example, by putting the patch of the present invention into a waterproof bag, followed by immersing the bag in hot water, such as a bath.

Hereinafter, the present invention will be more precisely explained by way of Examples; however, the present invention will not be limited to the examples.

EXAMPLE 1

As active components, extract of ginseng, extract of kelp, mink oil, extract of yeast, natural peppermint and natural salt were used. The active components and bases were warmed and mixed at a ratio as shown in Table 1 so as to obtain a paste-like adhesive mass. The thus-obtained adhesive mass was spread on a support made of cloth so as to obtain a large patch (20 cm×70 cm) in a cataplasm-like form.

Ten volunteer women used the thus-obtained patch as follows: The patch was put into a bag made of vinyl and the bag containing the patch was immersed in a bath so as to warm the patch while the woman bathed. After taking a bath in the evening, the warmed patch was taken out of the bag, and swathed around the abdominal region. The women passed the evening and the night as usual with the patch swathed. The patch was kept swathed until the next morning and then removed. This was repeated for 30 days. The women were not subjected to any special diet during the experiment. The feeling after 30 days of use is summarized in Table 2. Further, the size of the waists of the women was measured before and after treatment. The change of waist size is shown in Table 3.

COMPARATIVE EXAMPLE 1

In comparative example 1, no active components were added. The amount of the bases is shown in Table 1. The patch was prepared in the same manner as in Example 1, and used in the same manner as in Example 1 by ten women. The women were not subjected to any special diet during the experiment. The feeling after 30 days of use was summarized in Table 2. Further, the size of the waists of the women was measured before and after treatment. The change of waist size is shown in Table 3.

COMPARATIVE EXAMPLE 2

In comparative example 2, the active components of Example 1 were used in an amount double that of Example 1. To these active components, 1% by weight of gelatin, 10% by weight of glycerol and 85.4% by weight of purified water were added and mixed so as to obtain a viscous liquid. The components are summarized in Table 1. Ten women rubbed 5 ml of this liquid directly on the abdominal region once a day after they took a bath. This was continued for 30 days. The women were not subjected to any special diet during the experiment. The feeling after 30 days of use is summarized in Table 2. Further, the size of the waists of the women was measured before and after treatment. The change of waist size is shown in Table 3.

TABLE 1

| | Content of Active Components in the Adhesive Mass of the Patch | | |
|---|---|---|---|
| Component | Example 1 | Comparative Example 1 | Comparative Example 2 |
| Base | | | |
| gelatin | 5.0 | 5.5 | 1.0 |
| polyvinyl alcohol | 3.0 | 3.0 | — |
| carboxymethylcellulose | 3.0 | 3.5 | — |

TABLE 1-continued

Content of Active Components in the
Adhesive Mass of the Patch

| Component | Example 1 | Comparative Example 1 | Comparative Example 2 |
|---|---|---|---|
| glycerol | 25.0 | 26.0 | 10.0 |
| kaolin | 10.0 | 10.5 | — |
| sodium polyacrylate | 2.5 | 2.5 | — |
| Active components | | | |
| extract of ginseng | 1.0 | — | 2.0 |
| extract of kelp | 0.5 | — | 1.0 |
| mink oil | 0.5 | — | 1.0 |
| extract of yeast | 0.5 | — | 1.0 |
| natural peppermint oil | 0.1 | — | 0.2 |
| natural salt | 1.0 | — | 2.0 |
| Purified water | 47.9 | 49.0 | 81.8 |
| Total | 100.0 | 100.0 | 100.0 |

(the numbers indicate % by weight)

TABLE 2

Feeling After 30 bays of Use of the Plaster
Which Swathed the Abdominal Region

| Feeling of Use | Example 1 | Comparative Example 1 | Comparative Example 2 |
|---|---|---|---|
| skin feels full of life | 8 | 1 | 4 |
| skin feels tightened | 7 | 1 | 3 |
| skin feels moisturized | 9 | 2 | 5 |
| feel slenderized | 5 | 0 | 2 |
| no change | 0 | 6 | 2 |

(the numbers indicate the number of person and overlapping answers are included)

TABLE 3

Change in Waist Size after 30 Days

| Change in Size | Example 1 | Comparative Example 1 | Comparative Example 2 |
|---|---|---|---|
| −1 cm | 4 | 1 | 3 |
| −2 cm | 3 | 0 | 1 |
| −3 cm | 2 | 0 | 0 |
| no change | 1 | 9 | 6 |

(the numbers indicate the number of person)

As clearly shown in Table 2, the patch of Example 1 of the present invention which includes active components is superior in its skin-refreshing effect and skin-clearing effect as compared with that of Comparative example 1, which does not include active components. Further, as shown in Table 3, the patch of the present invention is superior in its slenderizing effect. Moreover, although the viscous liquid of Comparative example 2 contains two times as much of the active components as that of Example 1, the effect of Comparative example 2 is inferior to that of Example 1. Therefore, the effect of the active components used in a patch form is greatly improved over that of the liquid form.

EXAMPLES 2 TO 6

Active components and the amounts thereof for each example are shown in Table 4. The base components of the adhesive mass was the same as that of Example 1. The total amount was adjusted by purified water. The active components and bases were warmed and mixed in the same manner as Example 1 so as to obtain a paste-like adhesive mass. The thus-obtained adhesive mass was spread on a support made of cloth to obtain a large patch (20 cm×70 cm) in a cataplasm-like form. The thus-obtained patch was warmed in the bath in the same manner as in Example 1. After taking a bath, the patch was swathed around the femoral region and left on for 30 minutes. This was repeated once a day, for 30 days. Each of the procedures of Examples 2 to 6 was conducted on ten volunteer women. The feeling after 30 days of use is summarized in Table 5. Further, the size of the circumference of the femoral region was measured before and after treatment. The change of size is shown in Table 6.

COMPARATIVE EXAMPLE 3

The patch of Comparative example 1, which does not contain active components, was used in the same manner as Examples 2 to 6 by ten women. The feeling after 30 days of use is summarized in Table 5. Further, the size of the circumference of the femoral region was measured before and after treatment. The change of size is shown in Table 6.

TABLE 4

Content of Active Components in the
Adhesive Mass of the Patch

| Component | Examples | | | | |
|---|---|---|---|---|---|
| | 2 | 3 | 4 | 5 | 6 |
| extract of ginseng | 1.0 | — | — | 1.0 | — |
| extract of adlay | — | 1.0 | — | — | 1.0 |
| extract of bud of Japanese honeysuckle | — | — | 1.0 | — | — |
| sesame oil | — | — | 0.3 | — | — |
| extract of kelp | 0.5 | — | 0.5 | — | 0.5 |
| extract of wakame seaweed | — | 0.5 | — | 0.5 | — |
| mink oil | 0.5 | — | — | — | 0.5 |
| horse oil | — | 0.5 | — | 0.5 | — |
| extract of abyssal shark | 0.5 | — | — | — | 0.5 |
| extract of yeast | — | — | 0.5 | — | — |
| extract of vegetable wasps | — | — | — | 0.3 | — |
| extract of chlorella | — | 0.5 | — | — | 0.5 |
| extract of shiitake mushroom | 0.5 | — | 0.5 | — | — |
| extract of natural peppermint | 0.1 | — | 0.1 | 0.1 | 0.1 |
| extract red pepper (5%) | — | 0.1 | 0.1 | 0.1 | — |
| mud of the Dead Sea | 5.0 | — | 5.0 | — | — |
| natural salt | — | 1.0 | — | 1.0 | 1.0 |

(the numbers indicate % by weight)

TABLE 5

Feeling After 30 Days of Use of the Plaster
Which Swathed the Femoral Region

| Feeling of Use | Examples | | | | | Comparative Example 3 |
|---|---|---|---|---|---|---|
| | 2 | 3 | 4 | 5 | 6 | |
| skin feels full of life | 9 | 8 | 8 | 8 | 9 | 2 |
| skin feels tightened | 7 | 6 | 8 | 6 | 8 | 3 |
| skin feels moisturized | 9 | 8 | 7 | 8 | 8 | 2 |
| feel slenderized | 6 | 4 | 7 | 5 | 6 | 1 |
| no change | 0 | 1 | 0 | 1 | 1 | 7 |

(the numbers indicate the number of person and overlapping answers are included)

TABLE 6

Change in Size of Circumference of
the Femoral Region after 30 Days of Use

| Change in | Examples | | | | | Comparative |
|---|---|---|---|---|---|---|
| Size | 2 | 3 | 4 | 5 | 6 | Example 3 |
| −0.5 cm | 3 | 2 | 3 | 3 | 4 | 2 |
| −1.0 cm | 2 | 4 | 2 | 3 | 3 | 0 |
| −1.5 cm | 2 | 1 | 2 | 1 | 1 | 0 |
| −2.0 cm | 1 | 0 | 1 | 1 | 0 | 0 |
| no change | 2 | 3 | 2 | 2 | 2 | 8 |

(the numbers indicate the number of person)

EXAMPLE 7

An adhesive mass was prepared using the components shown in Table 7 and a cataplasm-like patch was produced. For the base of the plaster, styrene/isoprene/styrene block copolymer (rubber) (purchased from Shell Chemical Co., Ltd.; Califlex (registered trademark) TR-1107) was used as the adhesive component; petroleum resin (purchased from Nihon Zeon Co., Ltd.; Kleyton (registered trademark) U-185, aliphatic type) was used as the auxiliary adhesion component; and polybutene was used as the softening agent. Toluene was added to these base components and heated so as to dissolve the components. After cooling, the active components were added and homogeneously mixed. The obtained mixture was applied to a release liner, followed by removing the toluene, and transferred to polyvinylchloride film, thereby obtaining a large cataplasm-like patch (15 cm×40 cm).

TABLE 7

Composition of the Adhesive Mass of the
Plaster-like Patch

| Component | % by weight |
|---|---|
| Base | |
| styrene/isoprene/styrene block copolymer | 37.0 |
| petroleum resin | 48.8 |
| polybutene | 9.0 |
| Active components | |
| extract of ginseng | 2.0 |
| extract of kelp | 1.0 |
| extract of yeast | 1.0 |
| natural peppermint oil | 0.1 |
| extract of red pepper (5%) | 0.1 |
| natural salt | 1.0 |
| Total (%) | 100.0 |

The thus-obtained cataplasm-like patch was used by ten volunteer women as follows: The patch was put into a bag made of vinyl and the bag containing the patch was immersed in a bath so as to warm the patch while the women bathed. After taking a bath in the evening, the warmed patch was taken out of the bag. The warmed patch was swathed around the arm a little tightly. They passed the evening and the night as usual with the patch swathed. The patch was kept swathed until the next morning and removed. This was repeated for 30 days. The women were not subjected to any special diet during the experiment. The feeling after 30 days of use is summarized in Table 8. Further, the size of the circumference of the arms of the women was measured before and after treatment. The change of size is shown in Table 9.

COMPARATIVE EXAMPLE 4

A cataplasm-like patch was prepared in the same manner as in Example 7 except that the adhesive mass did not contain the active components of Example 7. Ten volunteer women used the thus-obtained patch in the same manner as in Example 7. The women were not subjected to any special diet during the experiment. The feeling after 30 days of use was summarized in Table 8. Further, the size of the circumference of the arms of the women was measured before and after treatment. The change of size is shown in Table 9.

TABLE 8

Feeling After 30 Days of Use of the
Plaster Which Swathed the Arm

| Feeling of Use | Example 7 | Comparative Example 4 |
|---|---|---|
| skin feels full of life | 8 | 2 |
| skin feels tightened | 7 | 2 |
| skin feels moisturized | 6 | 0 |
| feel slenderized | 5 | 0 |
| no change | 1 | 7 |

(the numbers indicate the number of person and overlapping answers are included)

TABLE 9

Change in Size of Circumference
of the Arm after 30 Days

| Change in Size | Example 7 | Comparative Example 4 |
|---|---|---|
| −0.5 cm | 4 | 1 |
| −1.0 cm | 2 | 0 |
| −1.5 cm | 1 | 0 |
| no change | 3 | 9 |

(the numbers indicate the number of person)

As clearly shown in Tables 8 and 9, the skin-refreshing effect and skin-clearing effect of the cataplasm-like patch of the present invention on the arm are remarkable.

EXAMPLE 8

The patch used in Example 7 was cut into a tape having 5 cm width and 25 cm length. Ten volunteer women used this tape. After taking a bath in the evening, this tape was swathed around their ankles a little tightly and was used until the next morning. This was done once a day, for 30 days. The size of the ankle was measured before and after treatment. The change of size is shown in Table 10.

COMPARATIVE EXAMPLE 5

The patch used in Comparative example 4 that does not contain active components was cut into a tape having 5 cm width and 25 cm length. Ten volunteer women used this tape in the same manner as Example 8, for 30 days. The size of the ankle was measured before and after treatment. The change of size is summarized in Table 10.

TABLE 10

Change in Size of Circumference
of the Ankle after 30 Days

| Change in Size | Example 8 | Comparative Example 5 |
|---|---|---|
| −0.2 cm | 5 | 2 |
| −0.4 cm | 3 | 1 |
| −0.6 cm | 2 | 0 |
| no change | 1 | 7 |

(the numbers indicate the number of person)

As shown in Table 10, the skin-refreshing effect of the tape-form patch of the present invention on the ankle is remarkable.

EXAMPLE 9

Extract of ginseng, extract of *Hedera helix L*, extract of *Matricaria chamomilla L*, extract of *Rosmarinus officinalis L*, seaweed extract and l-menthol were used as active components. The active components and bases were mixed at a ratio as shown in Table 11 so as to obtain a paste-like adhesive mass. The thus-obtained adhesive mass was spread on a support made of cloth so as to obtain a patch of 10 cm×20 cm.

Twenty volunteer women used the thus-obtained patch as follows: after taking a bath in the evening, the patches were swathed around either the left arm or the right arm, either the upper portion of the left knee or the right knee, and either the left ankle or the right ankle. The patches were kept swathed until the next morning and removed. The patches were swathed for about 6 hours a day. This was repeated for 30 days. The feeling after 30 days of use is summarized in Table 12. Further, the size of the circumference of the swathed portion was measured before and after treatment. To decrease the scattering due to the increase or decrease of body weight, the size of the circumference of the unswathed portion of the arm, the unswathed upper portion of the knee and the unswathed ankle were also measured before and after treatment. The size of the arm was measured at a certain distance from the elbow. The sizes around the upper portion of the knee and the ankle were measured at a certain distance from the floor when the woman stood straight.

The change in size was measured as follows:

Size of change=(size of swathed portion after treatment−size of swathed portion before treatment)−(size of unswathed portion after treatment−size of unswathed portion before treatment).

Results are shown in Tables 13, 14 and 15.

COMPARATIVE EXAMPLE 6

A cataplasm-like patch was prepared in the same manner as in Example 9 except that the adhesive mass did not contain the active components of Example 9. Twenty volunteer women used the thus-obtained patch in the same manner as in Example 9. The feeling after 30 days of use and the change of size of the arm, upper portion of the knee and the ankle are shown in Tables 12, 13, 14 and 15, respectively.

TABLE 11

Content of Active Components in the
Adhesive Mass of the Patch

| Component | Example 9 | Comparative Example 6 |
|---|---|---|
| Base | | |
| gelatin | 5.0 | 5.5 |
| polyvinyl alcohol | 3.0 | 3.0 |
| carboxymethylcellulose | 3.0 | 3.5 |
| glycerol | 25.0 | 26.0 |
| kaolin | 10.0 | 10.5 |
| sodium polyacrylate | 2.5 | 2.5 |
| Active components | | |
| extract of ginseng | 5.0 | — |
| extract of *Hedera helix L.* | 3.5 | — |
| extract of *Matricaria chamomilla L.* | 2.0 | — |
| extract of *Rosamarinus officinalis L.* | 1.5 | — |
| seaweed extract | 1.0 | — |
| l-menthol | small amount | — |
| Purified water | 38.5 | 49.0 |
| Total (%) | 100.0 | 100.0 |

TABLE 12

Feeling After 30 Days of Use of the Plaster Which Swatched
the Arm, Upper Region of the Knee and the Ankle

| Feeling of Use | Example 9 | Comparative Example 6 |
|---|---|---|
| skin feels full of life | 16 | 4 |
| skin feels tightened | 10 | 1 |
| skin feels moisturized | 18 | 10 |
| feel slenderized | 10 | 2 |
| no change | 2 | 10 |

(the numbers indicate the number of person and overlapping answers are included.)

TABLE 13

Change in Size of Arm after 30 Days

| Change of Size | Example 9 | Comparative Example 6 |
|---|---|---|
| −0.5 ~ −1.0 cm | 2 | 0 |
| 0 ~ −0.5 cm | 12 | 3 |
| no change | 5 | 14 |
| 0 ~ −0.5 cm | 1 | 3 |
| Total (person) | 20 | 20 |

TABLE 14

Change in Size of the Upper Portion of
the Knee after 30 Days

| Change of Size | Example 9 | Comparative Example 6 |
|---|---|---|
| −0.5 ~ −1.0 cm | 6 | 1 |
| 0 ~ −0.5 cm | 8 | 4 |
| no change | 5 | 12 |
| 0 ~ 0.5 cm | 1 | 3 |
| Total (person) | 20 | 20 |

TABLE 15

Change in Size of the Ankle after 30 Days

| Change of Size | Example 9 | Comparative Example 6 |
|---|---|---|
| −0.5 ~ −1.0 cm | 8 | 1 |
| 0 ~ −0.5 cm | 8 | 2 |
| no change | 2 | 14 |
| 0 ~ 0.5 cm | 2 | 3 |
| Total (person) | 20 | 20 |

As is apparent from Table 12, the patch of Example 9 that contains active components is superior in its skin-refreshing effect and skin-clearing effect compared with that of Comparative example 6 which does not contain active components. Furthermore, as shown in Tables 13, 14 and 15, the patch of the present invention clearly has a slenderizing effect.

EXAMPLE 10

The adhesive mass obtained in Example 9 was spread on a support made of cloth so as to obtain a roll-like patch of 10 cm width.

The thus-obtained roll-like patch was used by 10 volunteer women as follows: The patch was put into a bag made of vinyl and the bag containing the patch was immersed in a bath so as to warm the patch while the woman bathed. After taking a bath, the warmed patch was swathed around the abdominal region and femoral region. The patches were kept swathed until the next morning and removed. The patches were swathed for about 6 hours a day. This was repeated for 30 days.

The feeling after 30 days of use is summarized in Table 16. Further, the size of the circumference of the swathed portion was measured before and after treatment. In the case of the femoral region, either the right or left femoral region was swathed. The size was measured in the same manner as in Example 9. Results are shown in Tables 17 and 18.

COMPARATIVE EXAMPLE 7

A roll-like patch was prepared in the same manner as in Example 10 except that the adhesive mass did not contain the active components of Example 10. Ten volunteer women used the thus-obtained patch in the same manner as in Example 10. The feeling after 30 days of use and the changes in size of the abdominal region and femoral region are shown in Tables 16, 17 and 18, respectively.

COMPARATIVE EXAMPLE 8

A liquid containing 1.5 times of the active components of Example 9 was prepared: that is, 7.5% by weight of extract of ginseng, 5.2% by weight of extract of *Hedera helix L*, 3.0% by weight of extract of *Matricaria chamomilla L*, 2.2% by weight of extract of *Rosmarinus officinalis L*, 1.5% by weight of seaweed extract and a small amount of l-menthol were mixed and used as active components. One percent by weight of gelatin, 10.0% by weight of glycerol and 69.5% by weight of purified water were added to the active components so as to prepare the liquid of Comparative example 8.

Ten volunteer women rubbed 5 ml of this liquid directly on the abdominal region and femoral region once a day after they took a bath. This was continued for 30 days. The feeling after 30 days of use and the change of size of the abdominal region and femoral region are shown in Tables 16, 17 and 18, respectively.

As is apparent from Table 16, the patch of Example 10 that contains active components is superior in its skin-refreshing effect and skin-clearing effect compared with that of Comparative example 7 which does not contain active components. Furthermore, as shown in Tables 17 and 18, the patch of the present invention clearly has a slenderizing effect. Moreover, Example 10, containing active components in a plaster, has superior effects in skin-refreshing, skin-clearing and slenderizing as compared with Comparative Example 8 which contains active components in a liquid, not in a plaster. It is recognized that active components are necessary to be included in a plaster in order to attain the skin-refreshing effect, skin-clearing effect and slenderizing effect.

TABLE 16

Feeling After 30 Days of Use of the Plaster Which Swathed the Abdominal Region and the Femoral Region

| Feeling of Use | Example 10 | Comparative Example 7 | Comparative Example 8 |
|---|---|---|---|
| skin feels full of life | 7 | 2 | 4 |
| skin feels tightened | 4 | 1 | 2 |
| skin feels moisturized | 9 | 5 | 5 |
| feel slenderized | 6 | 1 | 2 |
| no change | 1 | 5 | 3 |

TABLE 17

Change in Size of the Abdominal Region after 30 Days

| Change of Size | Example 10 | Comparative Example 7 | Comparative Example 8 |
|---|---|---|---|
| −2.0 ~ −3.0 cm | 1 | 0 | 0 |
| −1.0 ~ −2.0 cm | 3 | 0 | 1 |
| 0 ~ −1.0 cm | 4 | 1 | 2 |
| no change | 2 | 8 | 6 |
| 0 ~ 1.0 cm | 0 | 1 | 1 |
| Total (person) | 10 | 10 | 10 |

TABLE 18

Change in Size of the Femoral Region after 30 Days

| Change of Size | Example 10 | Comparative Example 7 | Comparative Example 8 |
|---|---|---|---|
| −1.5 ~ −2.0 cm | 1 | 0 | 0 |
| −1.0 ~ −1.5 cm | 2 | 0 | 0 |
| −0.5 ~ −1.0 cm | 2 | 0 | 1 |
| 0 ~ −0.5 cm | 3 | 2 | 2 |
| no change | 1 | 6 | 6 |
| 0 ~ 0.5 cm | 1 | 1 | 1 |
| 0.5 ~ 1.0 cm | 0 | 1 | 0 |
| Total (person) | 10 | 10 | 10 |

According to the present invention, active components that have a skin-refreshing effect, a skin-clearing effect and/or a slenderizing effect can be formed into a patch. The patch can be applied to the desired site of the body, and the active components can act effectively and sustainedly on the site of the body. The patch of the present invention is superior in the above effects compared with the conventional liquid-type product. Moreover, by making it into the patch form, the handling of the product becomes easier; the stickiness upon use of the product can be decreased; and the patch prevents clothes from getting dirty. Thus, the present invention is extremely useful for the purpose of skin refreshing, skin clearing and/or slenderizing the body.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A patch for beautification comprising a support and an adhesive mass, wherein the patch has at least one of a skin-refreshing effect, a skin-clearing effect and a slenderizing effect, and wherein the adhesive mass contains plant extracts, seaweed extracts, extract of peppermint, animal oil, mushroom extract and extract of pepper as active components.

2. The patch according to claim 1, wherein the adhesive mass contains extract of ginseng, extract of *Hedera helix L*, extract of *Matricaria chamomilla L*, extract of *Rosmarinus officinalis L*, seaweed extract and l-menthol as active components.

3. The patch according to claim 1, wherein the adhesive mass contains extract of ginseng, extract of adlay or extract of bud Japanese honeysuckle as the plant extract, extract of kelp or extract of wakame seaweed as the seaweed extract, mink oil or horse oil as the animal oil, extract of vegetable wasps or extract of shiitake mushroom as the mushroom extract, extract of chlorella as an algae extract, extract of natural peppermint as the plant extract, and extract of red pepper as the extract of pepper.

4. The patch according to claim 1, wherein the patch comprises extract of ginseng, extract of kelp, mink oil, extract of yeast, natural peppermint oil, and natural salt as active components.

5. The patch according to claim 2, wherein the patch is in the form of a cataplasm, plaster or tape.

6. The patch according to claim 2, wherein the patch can be applied to or can swathe a desired site of the body.

* * * * *

UNITED STATES PATENT AND TRADEMARK OFFICE
CERTIFICATE OF CORRECTION

PATENT NO. : 6,162,458
DATED : December 19, 2000
INVENTOR(S) : Masanori Asada et al.

It is certified that error appears in the above-identified patent and that said Letters Patent is hereby corrected as shown below:

Column 5, Line 25 "bays" should read --Days--.

Signed and Sealed this

First Day of May, 2001

Attest:

NICHOLAS P. GODICI

*Attesting Officer*  *Acting Director of the United States Patent and Trademark Office*